United States Patent [19]

Fischell et al.

[11] 4,294,264
[45] Oct. 13, 1981

[54] CERVIX-TO-RECTUM MEASURING DEVICE IN A RADIATION APPLICATOR FOR USE IN THE TREATMENT OF CERVICAL CANCER

[75] Inventors: David R. Fischell, Ithaca, N.Y.; Jeffrey C. Mazique, Mt. Rainier, Md.

[73] Assignee: The United States of America as represented by the Administrator of the National Aeronautics and Space Administration, Washington, D.C.

[21] Appl. No.: 796,258

[22] Filed: May 12, 1977

Related U.S. Application Data

[63] Continuation of Ser. No. 672,209, Mar. 31, 1976, abandoned.

[51] Int. Cl.³ .............................................. A61B 5/10
[52] U.S. Cl. ................................... 128/778; 128/1.2; 33/143 C
[58] Field of Search ................... 128/1.1, 1.2, 25, 774, 128/778; 33/174 D, 148 E, 143 C

[56] References Cited

U.S. PATENT DOCUMENTS

| | | | |
|---|---|---|---|
| 396,479 | 1/1889 | Green | 33/148 E |
| 673,944 | 5/1901 | Doty | 33/148 E |
| 1,295,327 | 2/1919 | Kaplan | 33/148 E |
| 1,317,708 | 10/1919 | Kaplan | 33/148 E |
| 1,621,778 | 3/1927 | Haglund | 33/148 E |
| 1,849,959 | 3/1932 | Schneider | 33/148 E |
| 2,544,939 | 3/1951 | Ritala | 128/1.2 |
| 3,740,779 | 6/1973 | Rubricuis | 33/174 D X |

*Primary Examiner*—Kyle L. Howell
*Attorney, Agent, or Firm*—Robert D. Marchant; John R. Manning; John O. Tresansky

[57] ABSTRACT

A cervix-to-rectum measuring device to be used in the treatment of cervical cancer which includes a handle and a probe pivotably connected to the handle for insertion in the rectum. The measuring device further includes means for coupling the handle to an intrauterine radiation applicator when the latter is positioned in the uterine cervix and the probe is inserted in the rectum to pivot the handle about the probe. A gear is provided which is adapted to pivot with the probe. A pinion pivotably connected to the handle meshes with the gear. A pointer fixed to the pinion is displaced in response to the pivoting of the handle about the probe, and this displacement can be read from a scale on the handle, providing an indication of the cervix-to-rectum distance.

1 Claim, 4 Drawing Figures

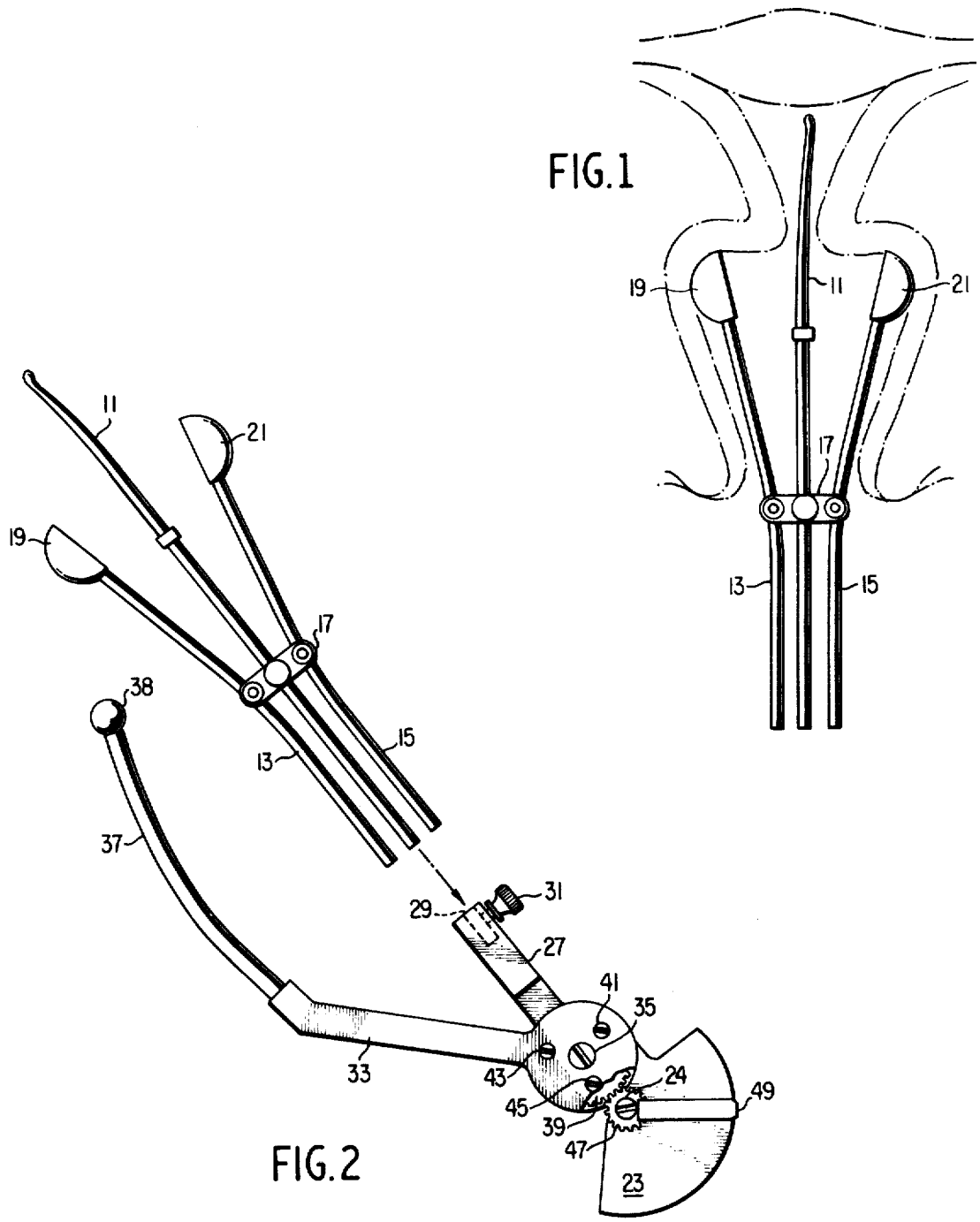

CERVIX-TO-RECTUM MEASURING DEVICE IN A RADIATION APPLICATOR FOR USE IN THE TREATMENT OF CERVICAL CANCER

ORIGIN OF INVENTION

The invention described herein was made in the performance of work under a NASA contract and is subject to the provisions of Section 305 of the National Aeronautics and Space Act of 1958, Public Law 85-568 (72 Stat. 435; U.S.C. 2457).

This is a continuation of application Ser. No. 672,209, filed Mar. 31, 1976 now abandoned.

BACKGROUND OF THE INVENTION

1. Field of the Invention

The present invention relates generally to radiation applicators for use in the treatment of cancerous tissue and, more particularly, to such an applicator having a measuring device to indicate the distance between the radiation sources and healthy tissues.

2. Description of the Prior Art

One of the most common sites of cancer in women is the uterine cervix, and it is customary to treat the cancer by irradiation with radioactive sources. A radioactive source applicator to which the present invention typically relates is the Henschke afterloading applicator described below. Typical patents directed to radioactive source applicators include:

U.S. Pat. No. 3,789,829
U.S. Pat. No. 3,323,511
U.S. Pat. No. 3,060,924
U.S. Pat. No. 2,888,917
U.S. Pat. No. 2,544,939.

The major problem with such devices is that they place the source of radioactivity so close to the rectum that it makes the rectal dose of radiation the limiting factor in the internal treatment. Thus, the rectal dose must be measured accurately to avoid over-irradiating the rectal area and harming healthy tissues in the process of treating diseased tissues.

To determine the rectal dose in most patients, the following procedure is followed. The radioactive source applicator is inserted and positioned in the vagina. A material not penetrated by X-rays is injected in the rectum, and an X-ray is then taken. The cervix-rectum distance is determined from the X-ray. This information along with the radioactive strength and position of each of the sources is fed into a computer. The computer determines the radiation levels in a series of what are called isodose curves. Isodose curves give a somewhat 3-dimensional view of the fall off of the radiation level with distance from the radioactive sources. The doctors can site the location of the rectum on this set of curves and thus estimate the rectal dose.

Among the problems associated with the isodose curve method are that the X-ray does not give an accurate measurement of the cervix-rectum distance measurement while it exposes the patient to additional radiation and requires computer facilities which are not always readily available.

For more accurate measurements there are several devices for determining the radiation level exactly. The first of these is an ion chamber which produces small pulses of current when the X-rays ionize the air inside. The pulses are so small they require a special preamplifier and counter. The second method used involves a scintillation detector, a material that takes in X-rays and turns out small amounts of visible light. The visible light is then light piped to a photo multiplier and then to a special counter. Both of these methods are expensive and somewhat complex and therefore do not afford simplicity and economy.

Because cervical cancer is a disease found, to a large degree, in underdeveloped countries, and in the lower economic communities of this country, any solution to this problem must be applicable to such areas where large and expensive facilities generally do not exist.

BRIEF SUMMARY OF THE INVENTION

It is therefore one object of the present invention to provide an improved radiation applicator for treatment of cancerous tissue in the uterine cervix.

It is another object to provide such an applicator wherein the cervix-to-rectum distance can be directly determined.

It is a further object to provide such an applicator where the means for determining the cervix-to-rectum distance can be coupled to the applicator and also positioned in the rectum without distorting the overall anatomy.

It is another object to provide such an applicator where the means for determining the cervix-to-rectum distance is simple to use and does not require additional instrumentation.

The objects of the present invention are achieved by providing a cervix-to-rectum measuring device in the radiation applicator. The measuring device includes a handle, a probe pivotably connected to the handle and insertable in the rectum, means for coupling the handle to the applicator when the latter is positioned in the uterine cervix and the probe is inserted in the rectum to pivot the handle about the probe, and means responsive to the pivoting of the handle for indicating the distance between the applicator and the tip of the probe, so that the cervix-to-rectum distance can be determined.

The foregoing as well as other objects, features and advantages of the present invention will become more apparent from the following detailed description taken in conjunction with the appended drawings.

BRIEF DESCRIPTION OF THE DRAWINGS

FIG. 1 is a top plan view of an afterloading radiation applicator being shown positioned in the vaginal tract and uterus, shown in section, to treat the uterus and cervix, including surrounding areas.

FIG. 2 is a top plan view of the unassembled afterloading radiation applicator and cervix-to-rectum measuring device.

DETAILED DESCRIPTION OF THE PREFERRED EMBODIMENTS

Figure 3:
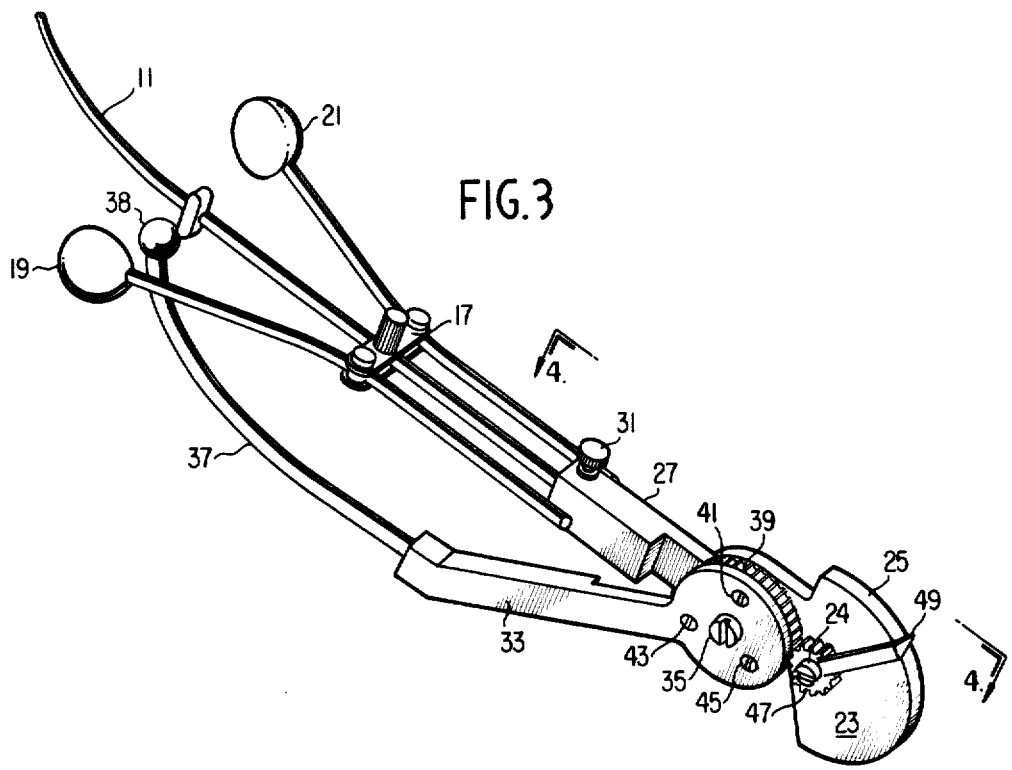
FIG. 3 is a perspective view of the assembled afterloading radiation applicator and cervix-to-rectum measuring device.

Referring now to the drawings, wherein like reference numerals designate identical elements, and more particularly to FIG. 1 there is illustrated the Henschke afterloading radiation applicator with which the cervix-to-rectum measuring device of the present invention has been incorporated. Since such applicators are well known in the field of radio-therapy and the use of the present invention need not be limited to this particular applicator it will be described only insofar as necessary to set forth the cooperative relationship of the cervix-to-rectum measuring device of the present invention.

The afterloading radiation applicator generally comprises a central tubular member 11 having a pair of pivotable hollow arms 13 and 15 connected thereto by a linkage 17. The applicator can be inserted in the vaginal tract, the central tubular member 11 and pivotable hollow arms 13 and 15 thereafter forming tubular containers to receive needles of radioactive material, such as cesium, radium or cobalt (not shown). The upper portion of the central tubular member 11 can be inserted into the uterine cervix so that the pivotable arms 13 and 15 lie adjacent to the cervix with their upper ends abutting the latter. The radioactive needle bearing portions of the pivotable arms 13 and 15 are provided with spherically shaped hoods 19 and 21 respectively of protective metal to shield portions of the anatomy which are not diseased.

Figure 4:
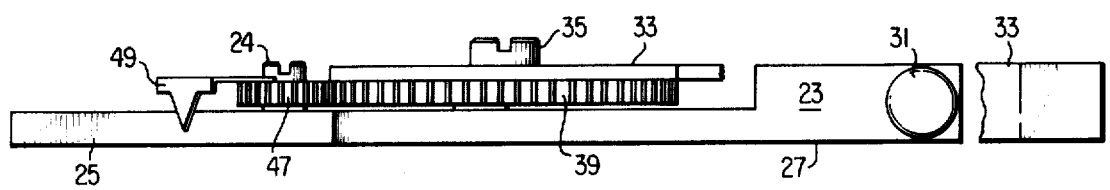
FIG. 4 is a side view of the cervix-to-rectum measuring device without the probe taken through line 3—3 of FIG. 3.

Referring to FIGS. 2, 3, and 4, there is illustrated the cervix-to-rectum measuring device of the present invention. The measuring device includes a handle 23 provided with a calibrated scale 25 at one end. The other end of the handle 23 is shaped as a shank 27 with a lengthwise cavity 29 for gripping with a set screw 31 the central tubular member 11 of the applicator. A probe arm 33 is pivotably mounted to the handle 23 by means of a shoulder screw 35. The probe arm 33 is fashioned to accommodate slender flexible rods or probes 37 of varying curvature. As more clearly shown in FIG. 4, a hubless gear 39 is secured in a recess in the underside of the probe arm 33 by machine screws 41, 43 and 45 (FIG. 2) and the probe arm and hubless gear turn about the pivot provided by the shoulder screw 35 so that the distance between the probe tip 38 and the central tubular member 11 of the applicator can be decreased or increased. A pinion 47 pivotably connected to the handle 23 by screw 24 and having a pointer 49 fixed thereto meshes with the hubless gear 39. When the probe arm 33 is turned, the pointer 49 is deflected and its displacement can be read from a scale 25. The numerals on the scale 25 indicate directly the distance between the probe tip 38 and the applicator.

In operation, the afterloading radiation applicator is first positioned in the uterine cervix. The probe tip 38 of the cervix-to-rectum measuring device is next inserted into the rectum. When the probe 37 is in place, the handle 23 of the measuring device is coupled to the central tubular member 11 of the afterloading applicator. The distance between the probe tip 38 and the central tubular member 11 of the applicator, which represents the cervix-to-rectum distance is then read on the calibrated scale 25 of the measuring device. The rectal dose is calculated, the measuring device is removed, and the radioactive needles are inserted in tubular containers 11, 13 and 15, of the afterloading applicator.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A device for use with a radiation applicator comprising:
   a handle,
   a single probe pivotably connected to said handle and insertable in a rectum,
   means on said handle for coupling said handle to the applicator, and
   means on said handle responsive to the displacement of said probe when inserted into a rectum relative to the applicator when inserted into an uterine cervix for indicating the distance between said cervix and rectum.

* * * * *